(12) United States Patent
Crombie et al.

(10) Patent No.: US 9,198,648 B2
(45) Date of Patent: Dec. 1, 2015

(54) METHOD AND DEVICE FOR APPROXIMATING TISSUE

(75) Inventors: John Stephen Crombie, East Hanover, NJ (US); James A. Fleming, III, Bethlehem, PA (US); Jessica Liberatore, Union City, CA (US); Jie Jenny Yuan, Neshanic Station, NJ (US); Robert Nering, Stockton, NJ (US)

(73) Assignee: ETHICON, INC., Somverville, NJ (US)

( * ) Notice: Subject to any disclaimer, the term of this patent is extended or adjusted under 35 U.S.C. 154(b) by 874 days.

(21) Appl. No.: 13/163,798

(22) Filed: Jun. 20, 2011

(65) Prior Publication Data

US 2012/0323275 A1    Dec. 20, 2012

(51) Int. Cl.
A61B 17/04        (2006.01)
A61B 17/06        (2006.01)
A61B 17/062       (2006.01)

(52) U.S. Cl.
CPC ............ *A61B 17/0401* (2013.01); *A61B 17/06* (2013.01); *A61B 17/062* (2013.01); *A61B 17/06114* (2013.01); *A61B 17/0483* (2013.01); *A61B 17/06138* (2013.01); *A61B 2017/0404* (2013.01); *A61B 2017/0409* (2013.01); *A61B 2017/0417* (2013.01); *A61B 2017/0475* (2013.01); *A61B 2017/0496* (2013.01); *A61B 2017/06142* (2013.01)

(58) Field of Classification Search
CPC .................. A61B 17/0401; A61B 2017/0417; A61B 2017/0416; A61B 2017/0409; A61B 17/06
USPC .................................. 606/139–142, 144, 232
See application file for complete search history.

(56) References Cited

U.S. PATENT DOCUMENTS

| 3,664,345 | A | | 5/1972 | Dabbs et al. |
| 3,910,181 | A | | 10/1975 | Andrews et al. |
| 3,910,281 | A | | 10/1975 | Kletschka et al. |
| 5,269,809 | A | | 12/1993 | Hayhurst et al. |
| 5,320,629 | A | | 6/1994 | Noda et al. |
| 5,788,063 | A | * | 8/1998 | Van Ness ..................... 206/63.3 |

(Continued)

FOREIGN PATENT DOCUMENTS

SU          1360705 A1    12/1987
WO    WO 2009/149455 A1   12/2009

(Continued)

OTHER PUBLICATIONS

Commercially available product called "g-Cath" sold by USGI Medical, Inc.; website http://www.usgimedical.com/eos/components-gcath.htm. (see cited USSN 7,942,884).

*Primary Examiner* — Gregory Anderson
*Assistant Examiner* — Christina Lauer

(57) ABSTRACT

A wound closure assembly and method for its use. The wound closure assembly includes a curved inserter having a distal end and a proximal end, a filamentary element extending between a proximal end and a distal end, wherein the proximal end is coupled to the proximal end of the curved inserter, a first anchor coupled to the filamentary element between its first and second ends, and a second anchor positioned at the distal end of the filamentary element. The filamentary element is configured to form a slip knot between the first and second anchors so as to enable the distance between the first and second anchors to be decreased by pulling on the proximal end of the filamentary element. The distal end of the curved inserter is received within a channel in the first anchor that extends along its longitudinal length.

23 Claims, 17 Drawing Sheets

(56) References Cited

U.S. PATENT DOCUMENTS

| | | |
|---|---|---|
| 6,635,073 B2 | 10/2003 | Bonutti |
| 6,702,835 B2 | 3/2004 | Ginn |
| 6,767,037 B2 * | 7/2004 | Wenstrom, Jr. ............... 289/1.2 |
| 7,153,312 B1 * | 12/2006 | Torrie et al. .................. 606/144 |
| 7,651,509 B2 | 1/2010 | Bojarski et al. |
| 7,713,285 B1 | 5/2010 | Stone et al. |
| 7,883,518 B1 | 2/2011 | Davies et al. |
| 7,942,884 B2 | 5/2011 | Vahid et al. |
| 2002/0019649 A1 | 2/2002 | Sikora et al. |
| 2002/0120292 A1 | 8/2002 | Morgan |
| 2003/0065402 A1 | 4/2003 | Anderson et al. |
| 2003/0088250 A1 | 5/2003 | Colleran et al. |
| 2004/0010287 A1 | 1/2004 | Bonutti |
| 2004/0162579 A1 | 8/2004 | Foerster |
| 2005/0187577 A1 | 8/2005 | Selvitelli et al. |
| 2006/0030884 A1 * | 2/2006 | Yeung et al. .................. 606/232 |
| 2006/0190042 A1 | 8/2006 | Stone et al. |
| 2007/0027475 A1 | 2/2007 | Pagedas |
| 2008/0140093 A1 | 6/2008 | Stone et al. |
| 2009/0024144 A1 | 1/2009 | Zeiner et al. |
| 2009/0024163 A1 | 1/2009 | Zeiner et al. |
| 2009/0082805 A1 | 3/2009 | Kaiser et al. |
| 2009/0088797 A1 * | 4/2009 | Crombie et al. ............... 606/232 |
| 2009/0222025 A1 | 9/2009 | Catanese, III et al. |
| 2009/0228042 A1 | 9/2009 | Koogle, Jr. et al. |
| 2009/0306776 A1 | 12/2009 | Murray |
| 2010/0114162 A1 | 5/2010 | Bojarski et al. |
| 2011/0022061 A1 | 1/2011 | Orphanos et al. |
| 2014/0088644 A1 | 3/2014 | Flint |

FOREIGN PATENT DOCUMENTS

| | | |
|---|---|---|
| WO | WO 2010/062743 A2 | 6/2010 |
| WO | WO 2012/151592 A2 | 11/2012 |

* cited by examiner

METHOD AND DEVICE FOR APPROXIMATING TISSUE

FIELD OF THE INVENTION

The present invention relates generally to the field of tissue approximation, and more particularly to a method and device for approximating tissue planes.

BACKGROUND

Separation of tissue planes is a common procedure in many different surgeries, such as, abdominalplasty, open ventral hernia repair, flap harvesting, deep tissue closure, and skin closure. After the tissue separation and completion of the surgery, the tissue planes must then be re-approximated. Although the goal is that the planes heal and reunite normally, it is often not the case, as seroma formation (fluid buildup) in the space between the tissue planes is a typical complication. When approximating tissue planes with traditional techniques, dead spaces are often formed between the tissue planes, which allows for tissue shear and subsequent seroma formation which in turn increases the risk of developing a seroma and an infection.

Attempts to minimize tissue seroma of this type include removal of the fluid from the space between the tissue planes using drains. Although somewhat effective, this method does not affect the formation of the fluid pockets, but rather removes the fluid as it is produced. Eliminating drains altogether is currently not considered an option. Other approaches attempt to minimize the likelihood of seroma formation and include alternative tissue fixation methods such as quilting sutures and progressive tissue suturing (PTS). Both quilting and PTS involve placing a large number of individual sutures progressively along the tissue planes, which is intricate are very time consuming These techniques also have other drawbacks, including accessibility, tension control, security, and consistency, and cheese-wiring.

What is needed is an improved device and method for approximating tissue planes that minimizes seroma formation and can be performed in a simple, quick, and efficient manner.

SUMMARY OF THE INVENTION

The present invention provides a wound closure assembly including a curved inserter having a distal end and a proximal end, a filamentary element extending between a proximal end and a distal end, wherein the proximal end is coupled to the proximal end of the curved inserter, a first anchor coupled to the filamentary element between its first and second ends; and a second anchor positioned at the distal end of the filamentary element. The filamentary element is configured to form a slip knot between the first and second anchors so as to enable the distance between the first and second anchors to be decreased by pulling on the proximal end of the filamentary element, and the distal end of the curved inserter is received within a channel in said first anchor, where the channel extends along a longitudinal length of the first anchor.

According to alternate embodiments, the first anchor may be slidably coupled to the filamentary element, and/or may include a tissue penetrating first end. Additionally, the first and second ends of the first anchor may be tapered. In yet another embodiment, the channel in the first anchor extends between first and second ends, and optionally, the distal end of the curved inserter may extend through the entire channel in the first anchor such that a tissue penetrating end of the curved inserter extends outwardly beyond the first end of the first anchor.

In yet another embodiment, the channel has a first portion and a second portion at least partially separated from the first portion, and wherein the filamentary element is positioned within the first portion and the distal end of the curved inserter is positioned within the second portion.

In yet another embodiment, the second anchor is a separate element coupled to the filamentary element, or optionally may be an enlarged or braided portion of the distal end of the filamentary element.

According to other alternate embodiments, the filamentary element may be a surgical suture made of polydioxanone; the curved inserter may be a suture needle; and/or the first and second anchors may be made of polydioxanone.

Also provided is a kit including a plurality of wound closure assemblies contained within a single package. Each wound closure assembly includes a curved inserter having a distal end and a proximal end, a filamentary element extending between a proximal end and a distal end, wherein the proximal end is coupled to the proximal end of the curved inserter, a first anchor coupled to the filamentary element between its first and second ends, and a second anchor positioned at the distal end of the filamentary element. The filamentary element is configured to form a slip knot between the first and second anchors so as to enable the distance between the first and second anchors to be decreased by pulling on the proximal end of the filamentary element, and the distal end of the curved inserter is received within a channel in the first anchor, where the channel extends along a longitudinal length of the first anchor.

The present invention also provides a method for approximating first and second tissue segments including the steps of grasping a wound closure assembly including a curved inserter having distal and proximal ends, a filamentary element coupled to the proximal end of the curved inserter and extending to a distal end, and first and second anchors coupled to the filamentary element, the filamentary element being configured to form a slip knot between the proximal and distal ends. The method further includes coupling the first anchor to the distal end of the curved needle, penetrating the first tissue segment then the second tissue segment with a first end of the first anchor while coupled with the distal end of the curved inserter, such that the first anchor becomes embedded in the second tissue segment, retracting the curved inserter from the second then first tissue segments, leaving the first anchor embedded in the second tissue segment, and pulling on the proximal end of the filamentary element to cause the slip knot to slide along the filamentary element, thereby causing the distance between the first and second anchors to be reduced to thereby approximate the first and second tissue segments.

The coupling step of the method may be inserting the distal end of the curved inserter within a channel extending at least partially through the first anchor. The channel may optionally extend through the first anchor, with the filamentary element extending through the channel so as to slidably couple the first anchor to the filamentary element.

The filamentary element, and first and second anchors may be made of a bioabsorbable material, such as polydioxanone.

Also provided is a wound closure assembly including a curved inserter having a distal end and a proximal end, a filamentary element extending between a proximal end and a distal end, a first anchor coupled to the filamentary element between its first and second ends, and a second anchor positioned in proximity to the distal end of the filamentary element. The filamentary element is configured to form a slip knot between the first and second anchors so as to enable the distance between the first and second anchors to be decreased by pulling on the proximal end of the filamentary element, and the distal end of the curved inserter is receivable within a channel that extends along a longitudinal length of the first anchor to thereby removably couple the curved inserter to the first anchor.

These and other objects, features and advantages of the present invention will be apparent from the following detailed description of illustrative embodiments thereof, which is to be read in connection with the accompanying drawings.

BRIEF DESCRIPTION OF THE DRAWINGS

FIG. 9e illustrates an alternate embodiment of the present invention including an additional pull ring or the like;

DETAILED DESCRIPTION

Figure 1:
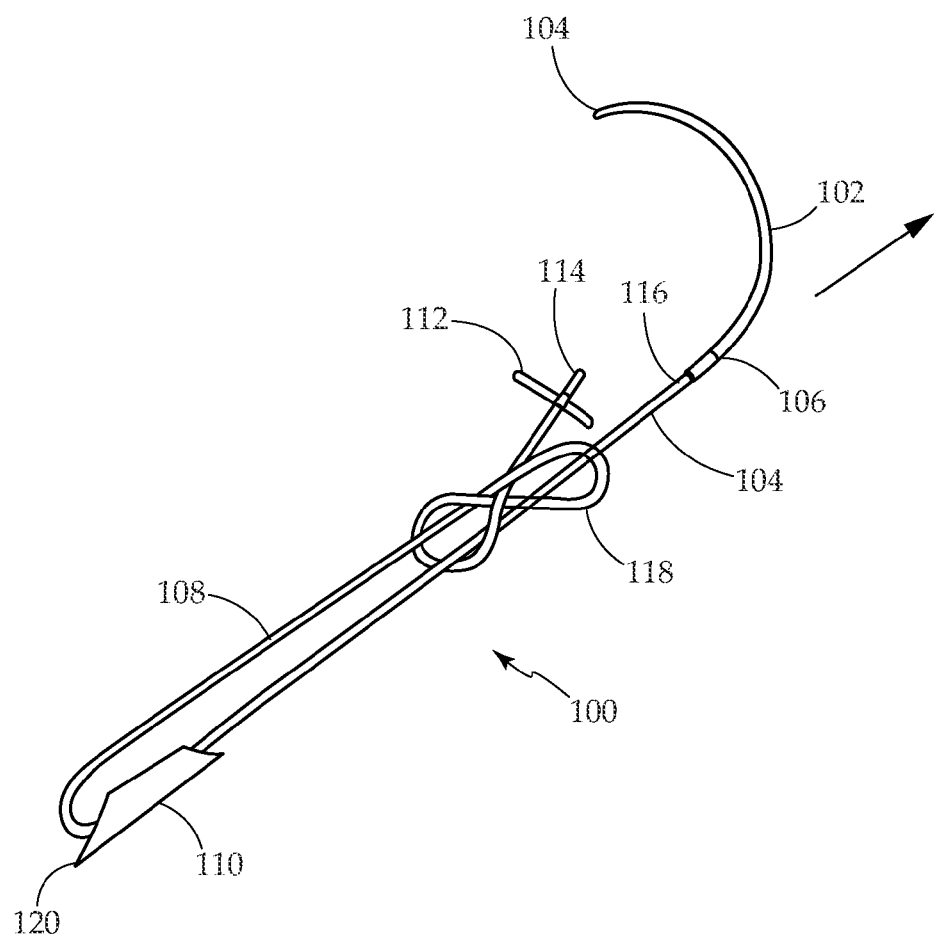
FIG. 1 illustrates a wound closure assembly according to the present invention.

FIG. 1 illustrates an exemplary embodiment of a wound closure assembly 100 according to the present invention. The wound closure assembly 100 includes a curved inserter 102 having a distal end 104 and a proximal end 106, with the proximal end being coupled to a filamentary element 108. The curved inserter 102 may be a standard surgical needle used to insert sutures. Although the illustrated embodiment of the curved inserter 102 has a pointed distal end 104, it will be apparent from the description below that the distal end of the inserter is not needed for penetrating tissue, and thus may be blunt as well.

A first anchor 110 and a second anchor 112 are coupled to the filamentary element along its length. The first anchor 110 is slidably coupled to the filamentary element so as to be slidable along its length, preferably by threading the filamentary element through channel 124 as will be described further below. The second anchor is fixedly secured to a distal end 114 of the filamentary element as illustrated. The filamentary element is configured so as to form a "slip knot" 118 or the like between its proximal 116 and distal 114 ends. The term "slip knot" as used herein, is intended to mean any knot that can slip along the length of the filamentary element by pulling on one end of the filamentary element. Preferably, the slip knot 118 is positioned between the first and second anchors so as to enable the distance between the first and second anchors to be reduced by pulling on the proximal end 116 of the filamentary element (i.e., via the inserter) as shown by the arrow in FIG. 1. In this manner, tight approximation of tissue layers can be achieved.

Figure 2:
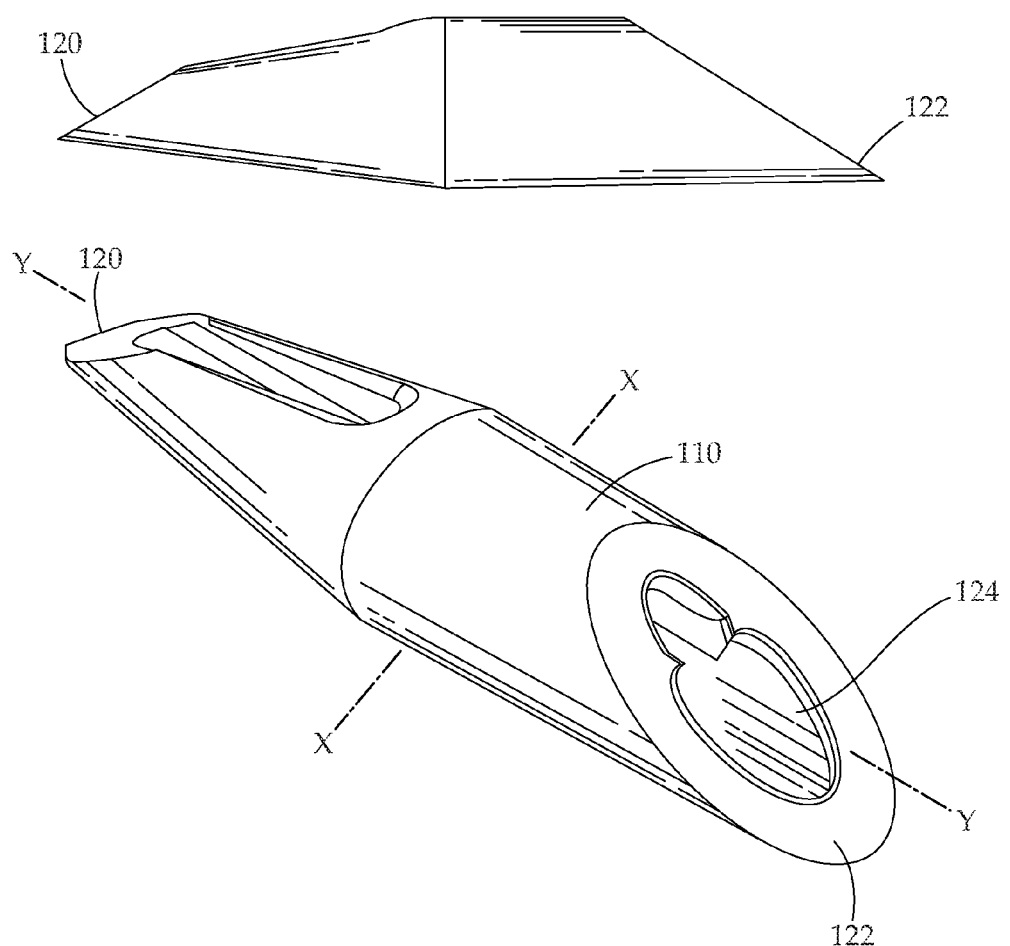
FIG. 2 illustrates a side view and perspective view of a first anchor of the wound closure assembly of FIG. 1.
Figure 3:
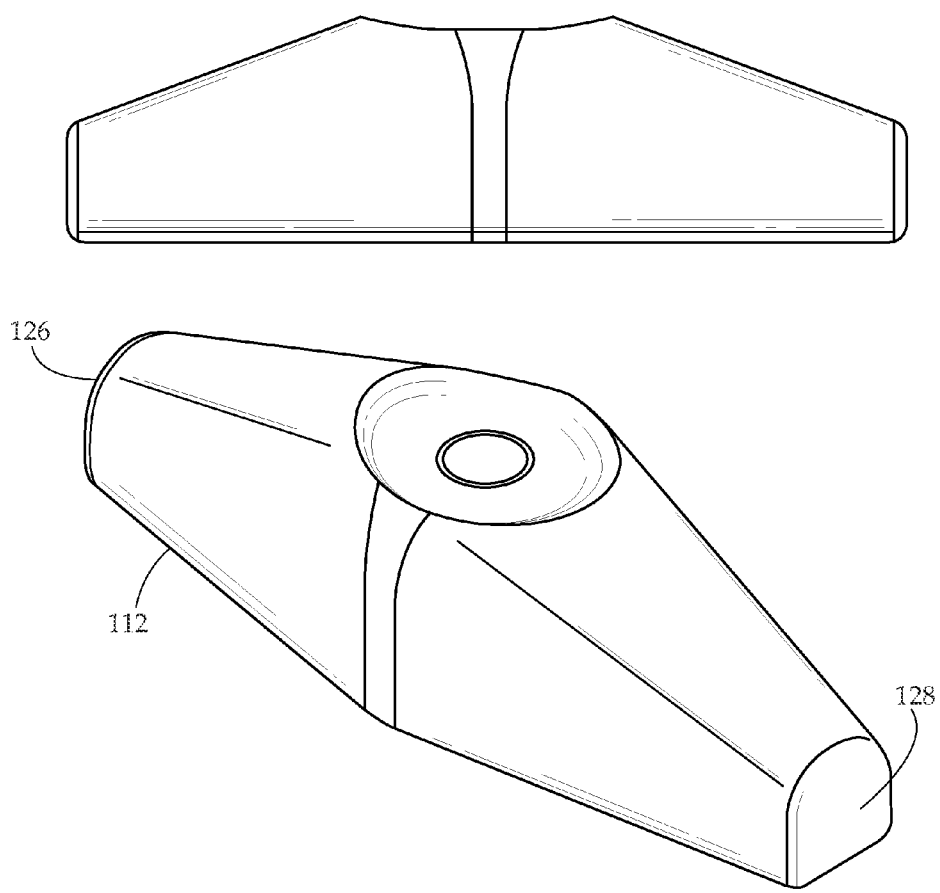
FIG. 3 illustrates a second anchor of the wound closure assembly of FIG. 1.
Figure 4:
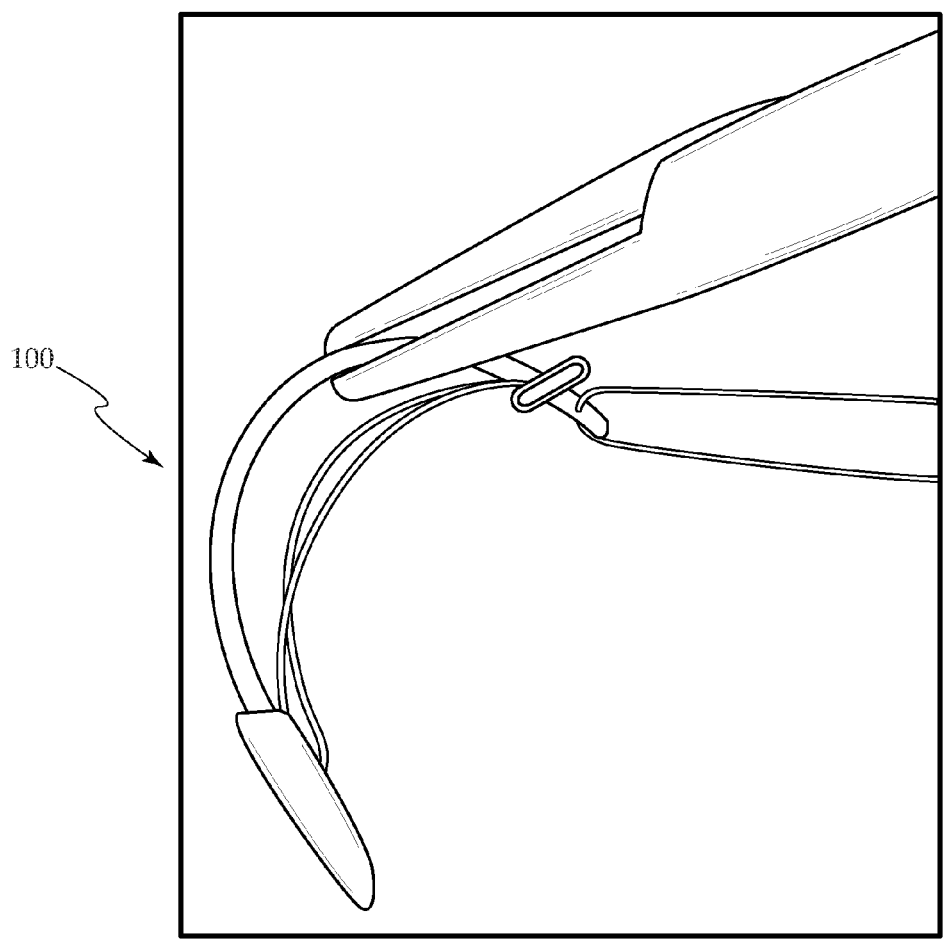
FIG. 4 illustrates the wound closure assembly of FIG. 1, as assembled for insertion into the body of a patient.
Figure 10:
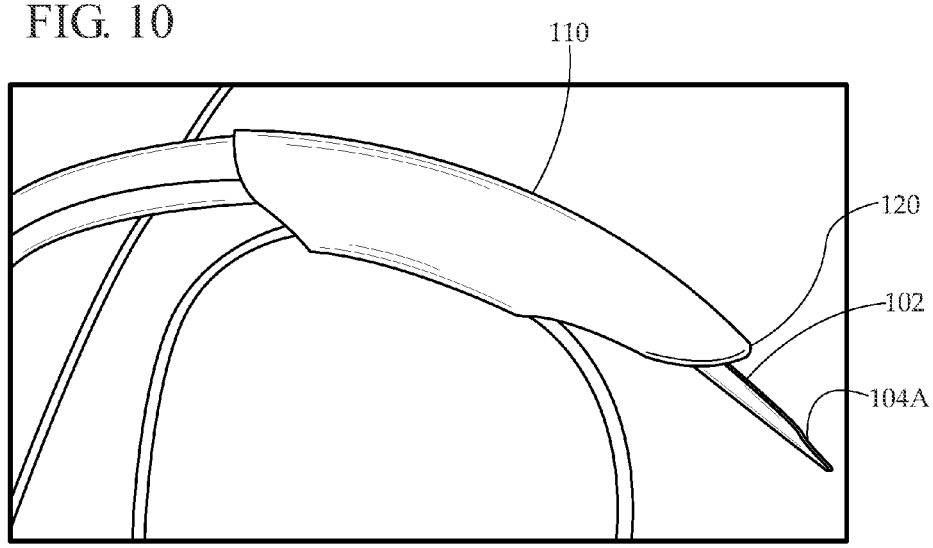
FIG. 10 illustrates an alternate embodiment of a wound closure assembly according to the present invention having a curved inserter extending entirely through the first anchor.
Figure 11:
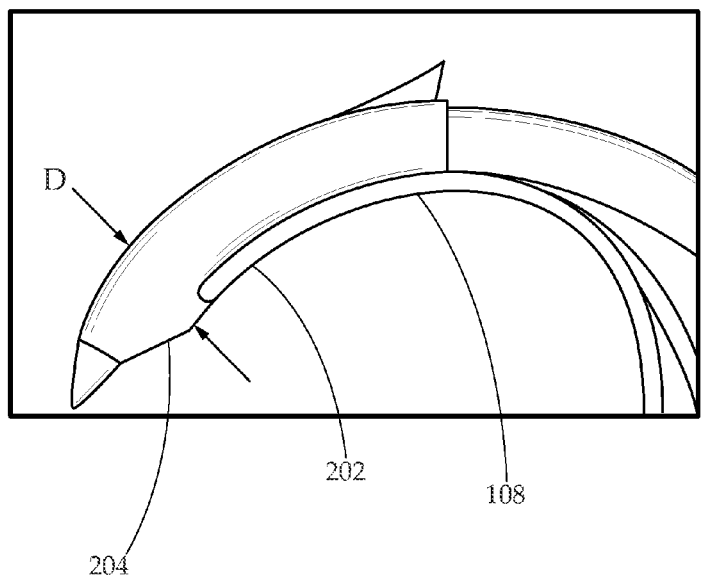
FIG. 11 illustrates an alternate embodiment of a first anchor according to the present invention.

Referring now to FIGS. 2 and 3, the first and second anchors 110, 112 are preferably made from a bioabsorbable polymer, such as polydioxanone (PDS), although any suitable biocompatible polymer (absorbable or non-absorbable) may be used. In a preferred embodiment, the first 120 and second 122 ends of the first anchor are tapered, with the first end 120 being sufficiently tapered so as to form a tissue penetrating end. The first anchor also has a channel 124 therethrough extending along the longitudinal length of the anchor between the first and second ends. As is better illustrated in FIG. 4, the channel 124 is sized and shaped to receive therein the distal end 104 of the inserter 102. Although in the preferred embodiment the distal end of the needle does not extend entirely through the channel, in an alternate embodiment shown in FIG. 10, it does so as to allow a pointed distal end 104a of the inserter 102 to extend outwardly from the first end 120 of the anchor 110 to facilitate tissue penetration as the assembly is being inserted. In either embodiment, the first anchor 110 may further include a recessed section 202 just distal of a tapered leading end 204, with the recessed section being designed to allow the filamentary element 108 to be shielded por positioned behind the tapered leading end 204 so that when inserted through tissue, the presence of the filamentary element does not further widen the insertion tract beyond the outer diameter D of the first anchor, as shown in FIG. 11.

Figure 5:
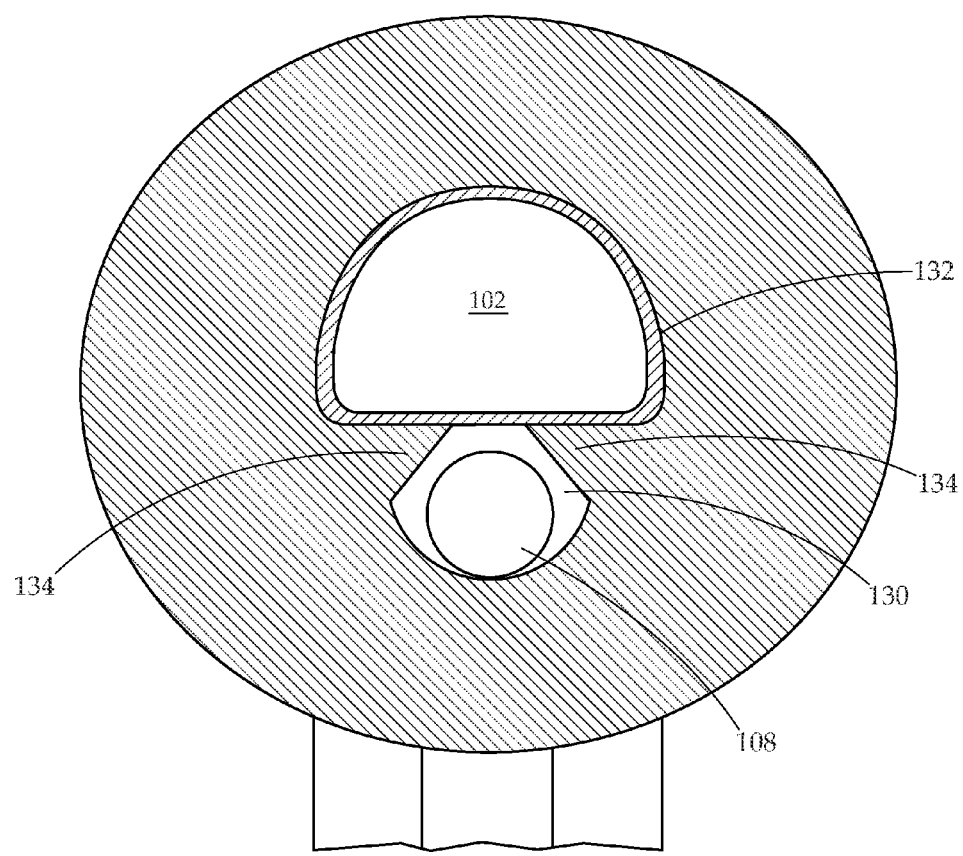
FIG. 5 is a cross-sectional view of the first anchor of FIG. 2.
Figure 5A:
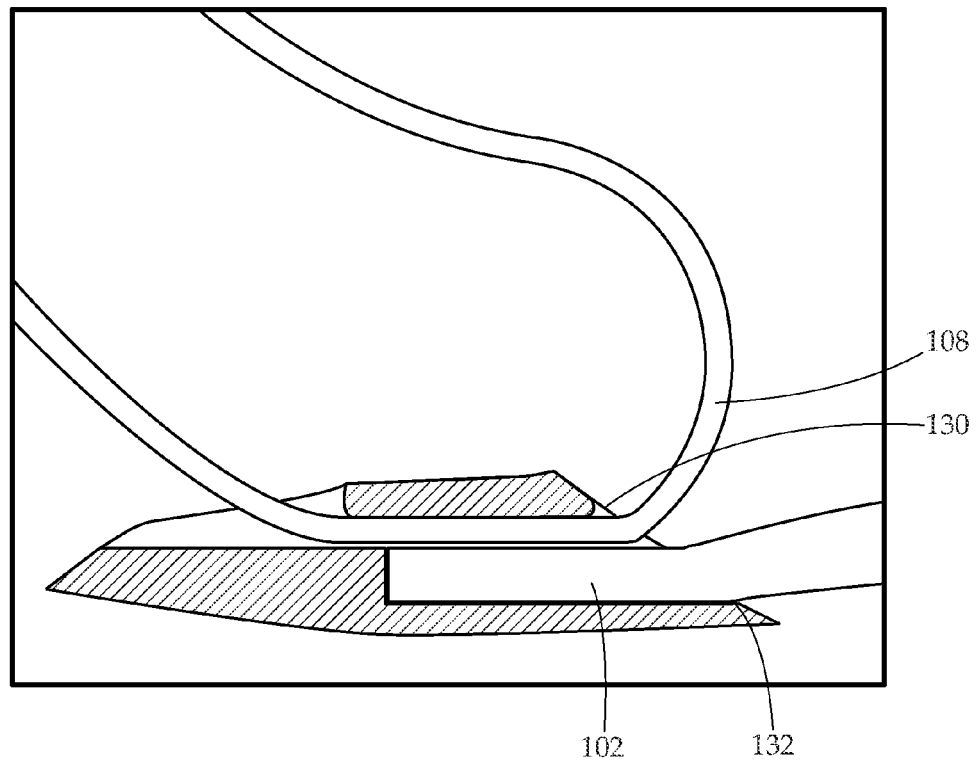
FIG. 5a is a cross-sectional side view of the first anchor coupled with an inserter.

FIG. 5 is a cross-section of the first anchor illustrating the channel 124. In this preferred embodiment, the channel 124 is separated into first 130 and second 132 sections, partially separated by extensions 134. The filamentary element 108 extends through the first section 130, and the second section is sized and shaped to receive the distal end of the curved inserter 102. The second section may include additional features for more securely engaging the distal end of the inserter. For example, the second section of the channel may decrease along its length to form a tight interference fit with the distal end of the inserter. The circumference of the second section may also (or alternatively) include one or more projections 135 or the like designed to engage a corresponding recess in the distal end of the inserter (not shown).

Figure 8:
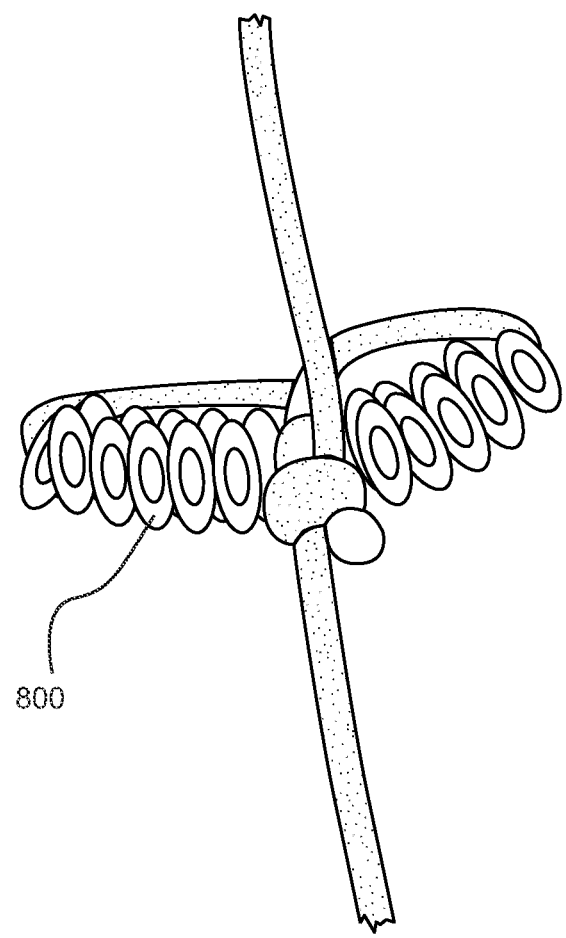
FIG. 8 illustrates an alternate embodiment of the second anchor of a wound closure assembly according to the present invention.

The second anchor 112 acts as a stopper as is further described below, and preferably includes blunt or rounded first and second ends 126, 128. Although in the illustrated embodiment the second anchor is a separate element secured to the distal end of the filamentary element, alternatively, the second anchor can be formed integrally with the distal end of the filamentary element, such as by braiding or otherwise winding the distal end of the filamentary element to form the enlarged stop. An example of such a stop is shown in FIG. 8.

Figure 7:
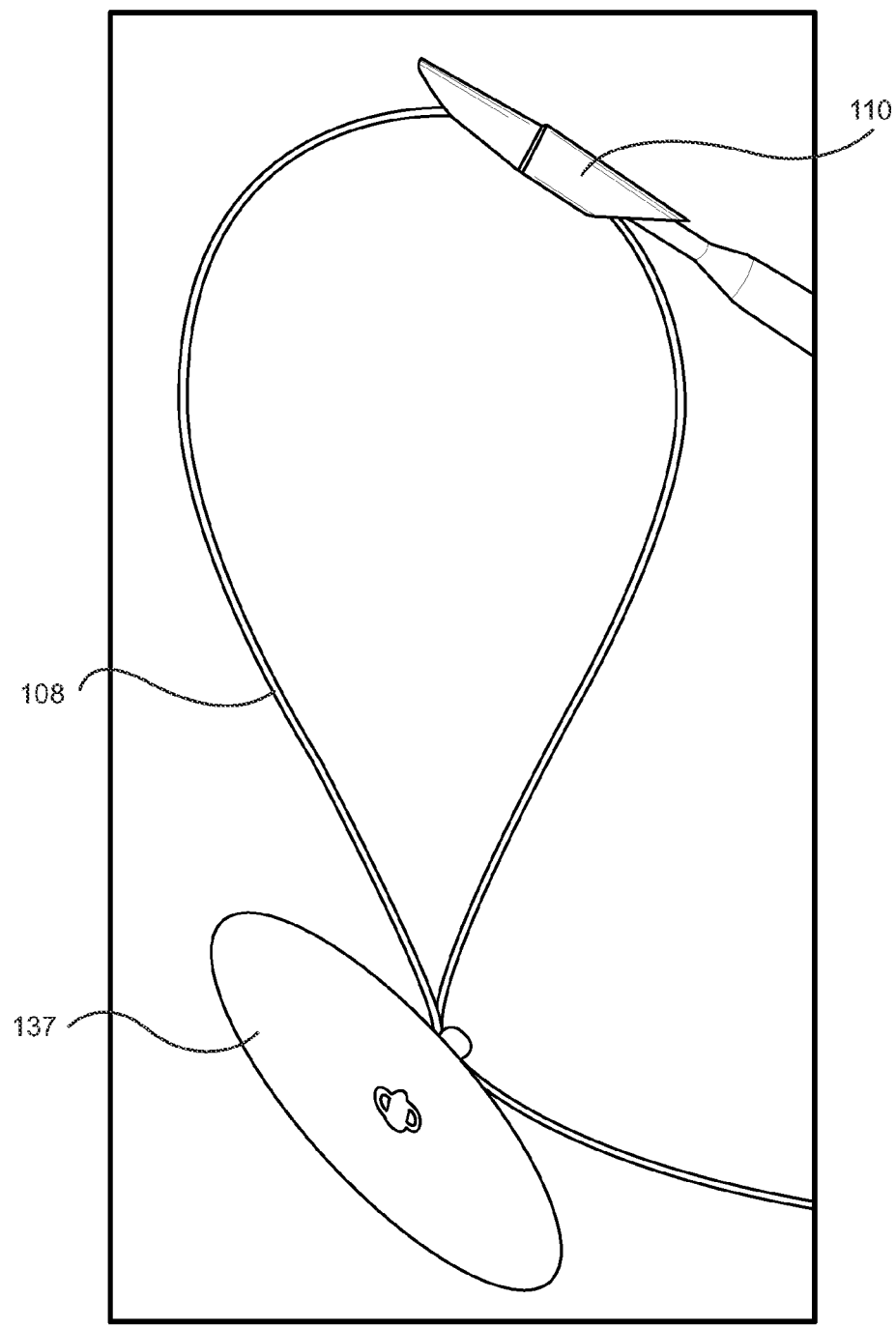
FIG. 7 illustrates an alternate embodiment of a wound closure assembly according to the present invention.

Further, the second anchor may be comprised of something other than a solid biocompatible polymer, such as a mesh disc-shaped element 137 as shown in FIG. 7, which would promote tissue in-growth.

Figure 9A:
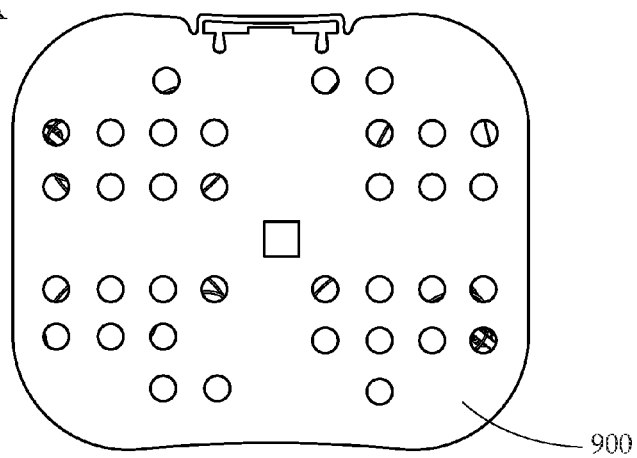
FIGS. 9a and 9b illustrate multiple wound closure assemblies according to the present invention within a package in the closed and open positions respectively.
Figure 9B:
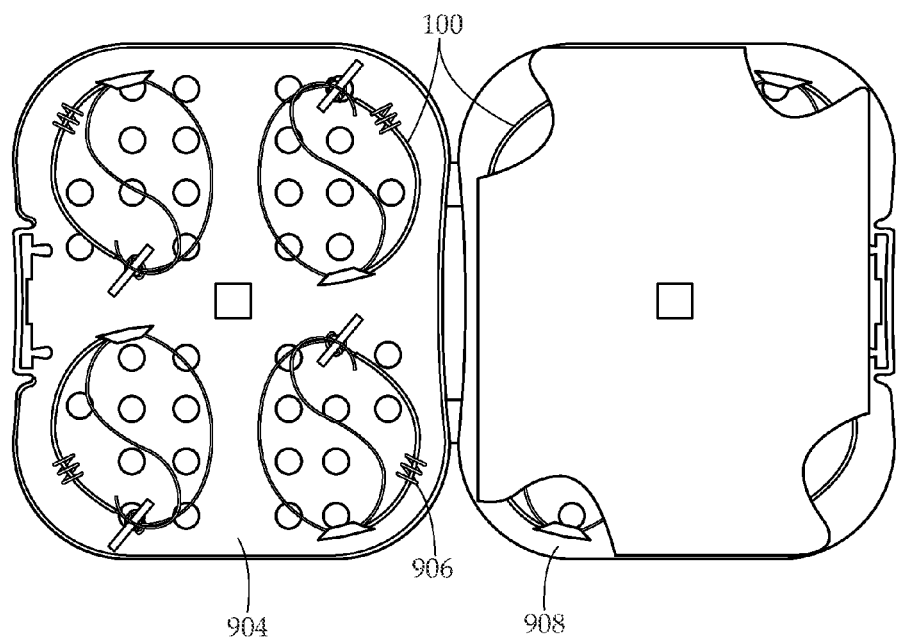
Figure 9C:
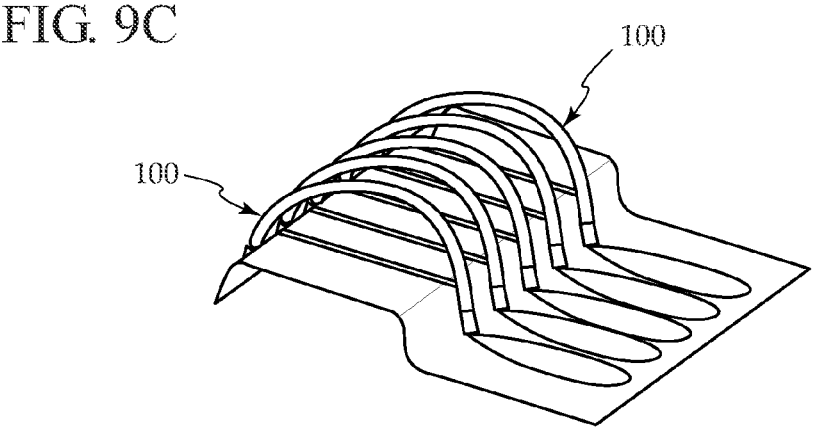
FIGS. 9c and 9d illustrate alternate embodiments for packaging multiple wound closure assemblies according to the present invention.
Figure 9D:
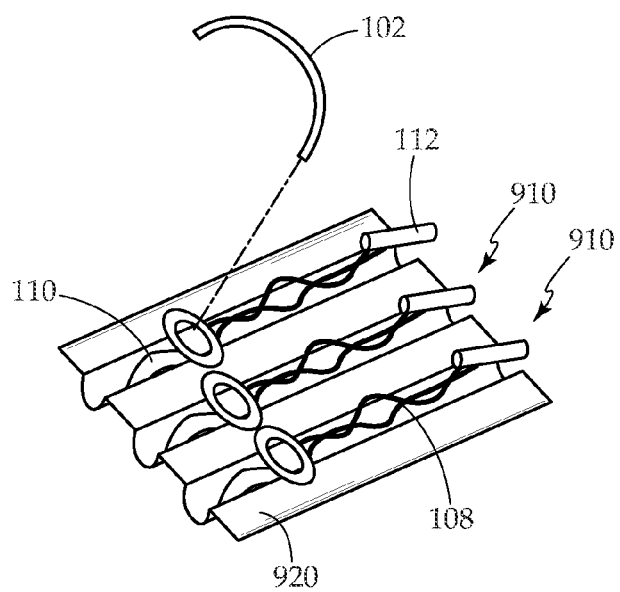
Figure 9E:
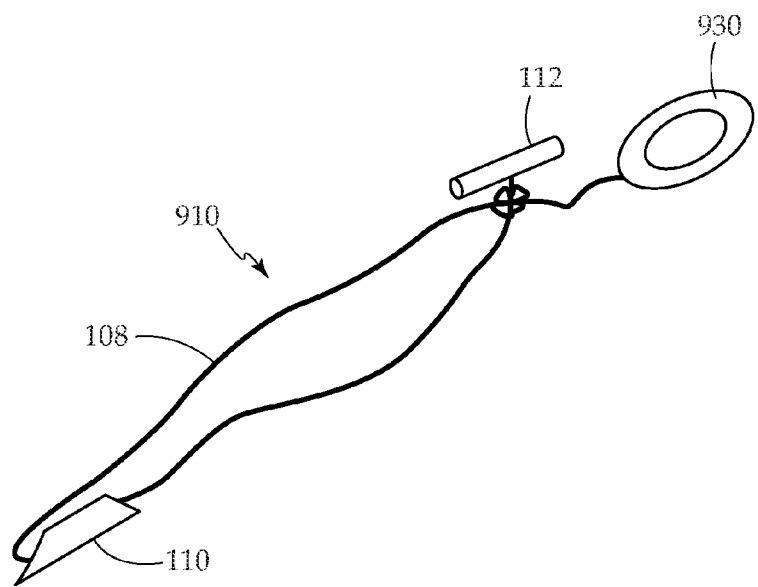

The wound closure assemblies according to the present invention may be provided to surgeons individually packages, or in a package containing multiple assemblies as shown in FIGS. 9a and 9b. FIG. 9a illustrates a molded plastic package 900 in the closed position and containing eight wound closure assemblies. FIG. 9b illustrates the same package in the open position illustrating two sets of fours assemblies, separated by a divider 902 or the like. The first four are positioned spaced apart from one another and secured to the top cover 904 by holding tabs 906 or the like, whereas the second four are similarly positioned and secured to the bottom cover 908. Alternatively, multiple wound closure assemblies 100 may be positioned side by side within a package as shown in FIG. 9c. FIG. 9d illustrates yet another packaging embodiment wherein multiple anchor/filamentary element assemblies 910 are positioned side by side within a suitable package 920. The anchor/filamentary assemblies 910 are packaged separately from one or more inserters designed for use therewith. In this embodiment, the inserter is designed so as to be readily receivable within the channel 124 in the first anchor 110 of any of the anchor/filamentary element assemblies as they sit in the package. In this manner, the package functions as a cartridge holding multiple anchor/filamentary elements any one of which can readily be loaded onto the inserter for use. The anchor/filamentary element assemblies 910 may further include a pull ring 930 or the like as illustrated in FIG. 9e, suitable for assisting in drawing the first and second anchors together once implanted.

Figure 6A:
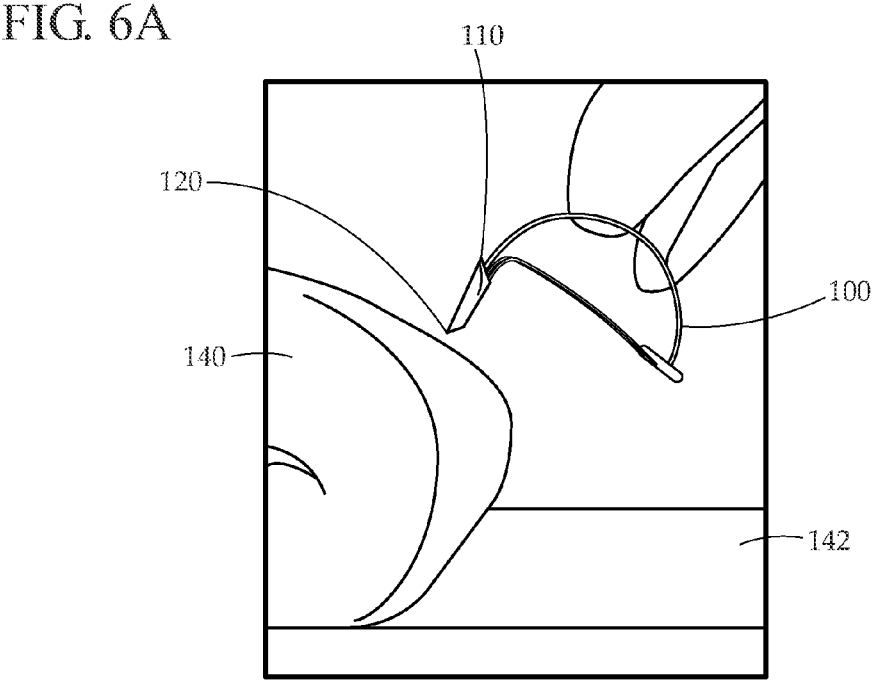
FIGS. 6a-6k illustrate various steps for approximating tissue planes using the assembly of FIG. 1.
Figure 6B:
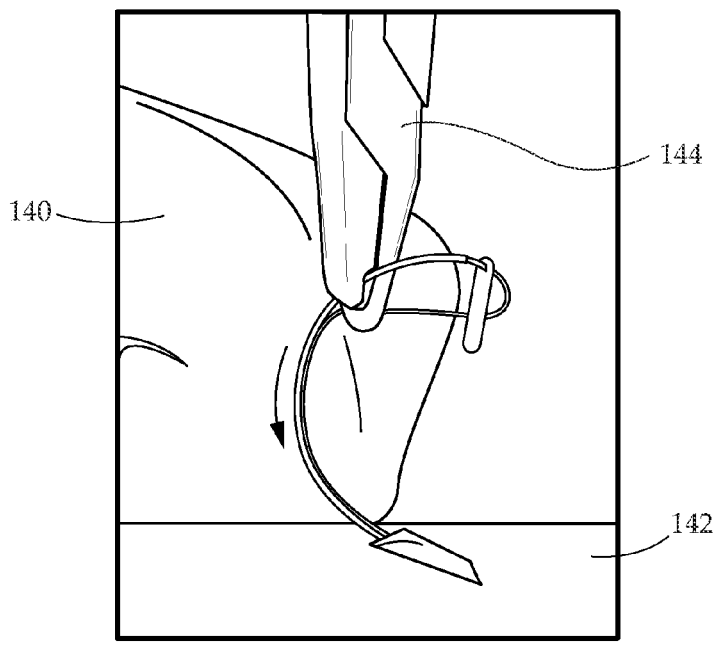
Figure 6C:
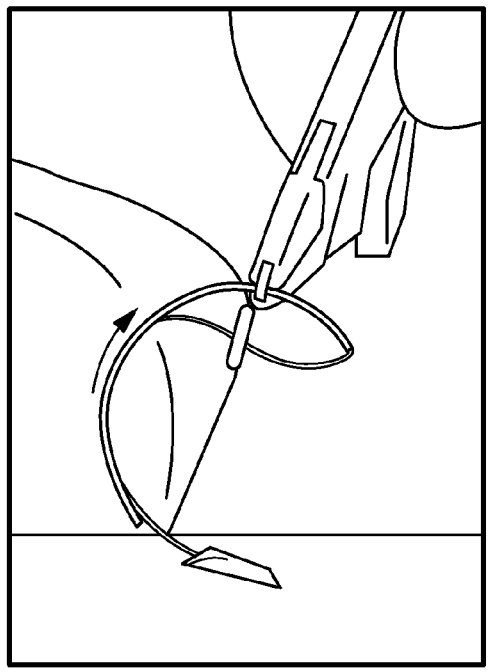
Figure 6D:
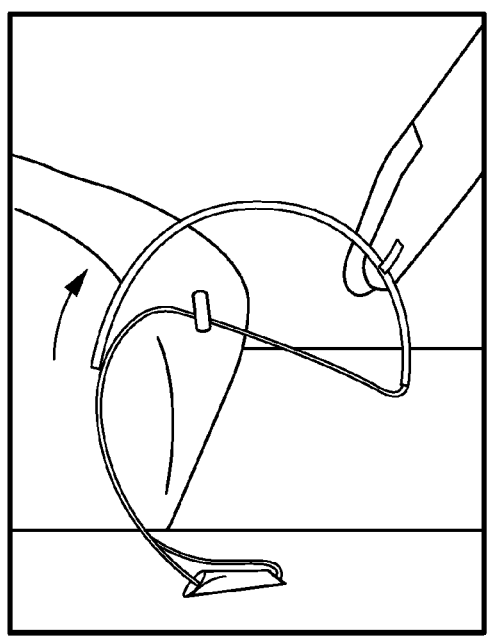
Figure 6E:
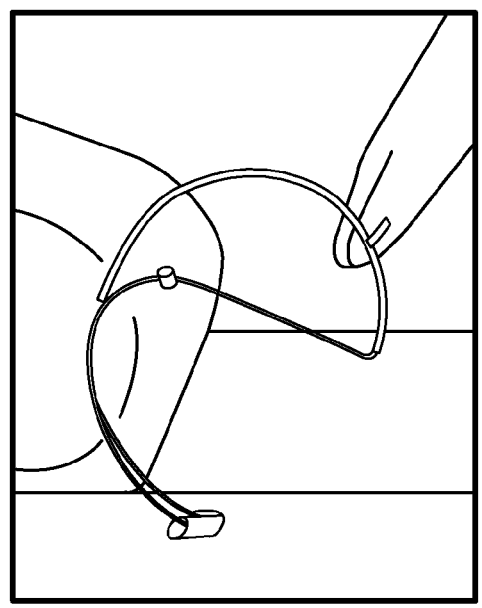
Figure 6F:
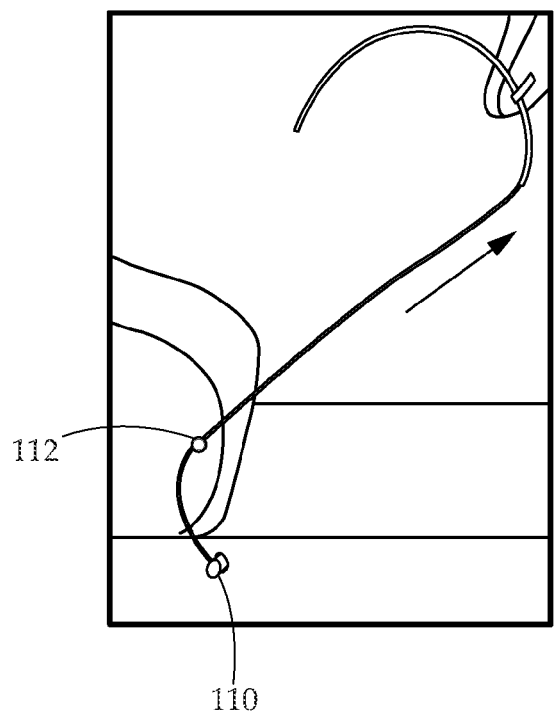
Figure 6G:
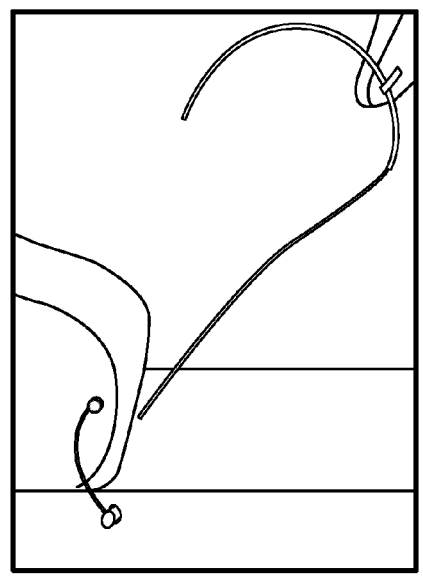
Figure 6H:
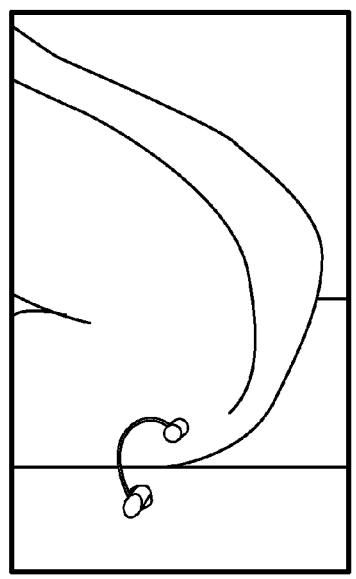
Figure 6I:
Figure 6J:
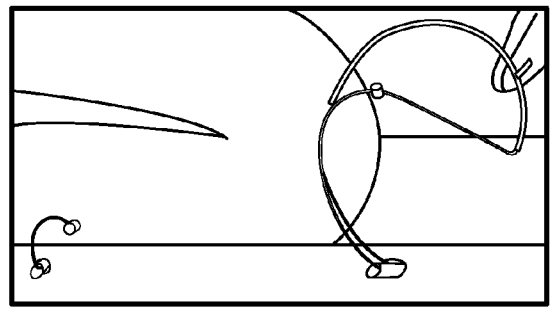
Figure 6K:
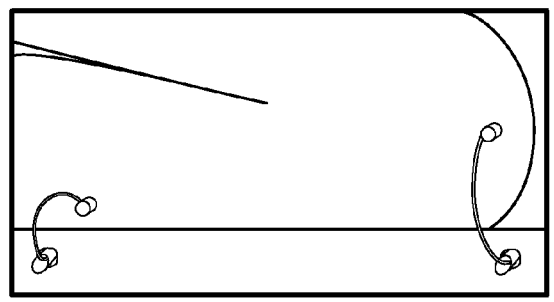

FIGS. 6a-6k illustrate various steps in a method for using the wound closure assembly to approximate first 140 and second 142 tissue planes. With the distal end of the inserter positioned within the channel 124 of the first anchor 110 as illustrated in FIG. 6a, the curved inserter 102 is grasped by the surgeon with a needle grasper 144 or the like, and positioned so that the tissue penetrating distal end 120 of the first anchor 110 is close to the first tissue flap 140. The wound closure assembly is then inserted through the first tissue flap and into the second tissue flap 142 so that that first anchor is within the second tissue flap as shown in FIG. 6b. The curved inserter is then retracted as shown by the arrow in FIGS. 6c and 6d. As the needle is retracted, the tapered end of the first anchor engages the tissue, causing the distal end of the needle to come uncoupled from the first anchor, leaving the first anchor embedded in the tissue as shown in FIGS. 6d and 6e. Once the inserter is entirely retracted from the tissue, the inserter is pulled in the direction indicated by the arrow in FIG. 6f, which, due to the slip knot 118, causes the second anchor 112 to be drawn closer to the first anchor 110 to thereby bring the tissue planes close together. The filamentary element is then cut in proximity to the tissue flap 140 as shown in FIG. 6g, leaving the first and second anchors and filamentary element therebetween, embedded in the tissue and approximating the tissue planes. These steps are then repeated using additional wound closure assemblies at successive intervals along the length of the tissue planes as illustrated in FIGS. 6i-6k.

The wound closure device of the present invention enables secure, quick, tissue plane approximation that greatly reduces fluid build-up and the resulting risk of seroma formation. The wound closure device can be inserted by a surgeon using a single hand and using familiar techniques (i.e., using common needle holders), leaving the other hand free to maintain positioning and tension on the tissue flap. Further, the present invention provides greatly increased speed over known PTS or suture quilting techniques, with each device taking approximately 6 seconds to place.

Although illustrative embodiments of the present invention have been described herein with reference to the accompanying drawings, it is to be understood that the invention is not limited to those precise embodiments and that various other changes and modifications may be effected herein by one skilled in the art without departing from the scope or spirit of the invention.

What is claimed is:

1. A wound closure assembly comprising:
   a curved inserter having a length extending along a curved path between a distal end and a proximal end;
   a filamentary element extending between a proximal end and a distal end, wherein the proximal end is fixedly coupled to the proximal end of the curved inserter;
   a first anchor coupled to the filamentary element between its the proximal and distal ends of the filamentary element; and
   a second anchor positioned at the distal end of the filamentary element;
   wherein the filamentary element is configured to form a slip knot between the first and second anchors so as to enable the distance between the first and second anchors to be decreased by pulling on the proximal end of the filamentary element via the curved inserter that is fixedly coupled thereto, and
   wherein the distal end of the curved inserter is received within a channel in said first anchor, said channel extending along a longitudinal length of said first anchor.

2. The wound closure assembly according to claim 1, wherein the first anchor is slidably coupled to the filamentary element.

3. The wound closure assembly according to claim 1, wherein the first anchor includes a tissue penetrating first end.

4. The wound closure assembly according to claim 3, wherein first and second ends of the first anchor are tapered.

5. The wound closure assembly according to claim 1, wherein the channel in the first anchor extends therethrough between first and second ends.

6. The wound closure assembly according to claim 5, wherein the distal end of the curved inserter extends through the entire channel in said first anchor such that a tissue penetrating end thereof extends outwardly beyond the first end of the first anchor.

7. The wound closure assembly according to claim 5, wherein the channel has a first portion and a second portion at least partially separated from the first portion, and wherein the filamentary element is positioned within the first portion and the distal end of the curved inserter is positioned within the second portion.

8. The wound closure assembly according to claim 1, wherein the second anchor is a separate element coupled to the filamentary element.

9. The wound closure assembly according to claim 1, wherein the second anchor is an enlarged or braided portion of the distal end of the filamentary element.

10. The wound closure assembly according to claim 1, wherein the filamentary element is a surgical suture comprised of polydioxanone, and wherein the curved inserter is a suture needle.

11. The wound closure assembly according to claim 1, wherein the first and second anchors are comprised of polydioxanone.

12. A kit comprising:
   a plurality of wound closure assemblies contained within a single package, wherein each wound closure assembly further comprises a curved inserter having a length extending along a curved path between a distal end and a proximal end, a filamentary element extending between a proximal end and a distal end, wherein the proximal end is fixedly coupled to the proximal end of the curved inserter, a first anchor coupled to the filamentary element between its first and second ends, and a second anchor positioned at the distal end of the filamentary element, wherein the filamentary element is configured to form a slip knot between the first and second anchors so as to enable the distance between the first and second anchors to be decreased by pulling on the proximal end of the filamentary element, and wherein the distal end of the curved inserter is received within a channel in said first anchor, said channel extending along a longitudinal length of said first anchor.

13. The kit according to claim 12, wherein the filamentary elements and first and second anchors are comprised of polydioxanone.

14. The kit according to claim 12, wherein each of the first anchors include a tissue penetrating first end.

15. The wound closure assembly according to claim 14, wherein first and second ends of each of the first anchors are tapered.

16. The wound closure assembly according to claim 15, wherein the channel in each of the first anchors extends therethrough between the first and second ends.

17. The wound closure assembly according to claim 16, wherein each channel has a first portion and a second portion at least partially separated from the first portion, and wherein the filamentary element of the respective wound closure assembly is positioned within the first portion and the distal end of the curved inserter is positioned within the second portion.

18. The wound closure assembly according to claim 12, wherein the second anchor is a separate element coupled to the filamentary element.

19. The wound closure assembly according to claim 12, wherein the second anchor is an enlarged or braided portion of the distal end of the filamentary element.

20. A wound closure assembly comprising:
a curved inserter having a length extending along a curved path between a distal end and a proximal end;
a filamentary element extending between a proximal end and a distal end, wherein the proximal end is fixedly coupled to the proximal end of the curved inserter;
a first anchor coupled to the filamentary element between its first and second ends;
a second anchor positioned in proximity to the distal end of the filamentary element;
wherein the filamentary element is configured to form a slip knot between the first and second anchors so as to enable the distance between the first and second anchors to be decreased by pulling on the proximal end of the filamentary element, and
wherein the distal end of the curved inserter is receivable within a channel that extends along a longitudinal length of the first anchor to thereby removably couple the curved inserter to the first anchor.

21. The wound closure assembly according to claim 20, wherein the first anchor is slidably coupled to the filamentary element.

22. The wound closure assembly according to claim 20, wherein the channel extends entirely through the first anchor, and wherein when removably coupled thereto, the distal end of the curved needle extends outwardly beyond the first end of the first anchor.

23. The wound closure assembly according to claim 22, wherein the curved needle further comprises a tissue penetrating distal end.

* * * * *